(12) United States Patent
Pastorello et al.

(10) Patent No.: US 6,642,213 B1
(45) Date of Patent: Nov. 4, 2003

(54) THREE-DIMENSIONAL PROSTHESES CONTAINING HYALURONIC ACID DERIVATIVES

(75) Inventors: Andrea Pastorello, Abano Terme (IT); Marco Radice, Formigine (IT); Lanfranco Callegaro, Thiene (IT)

(73) Assignee: Fidia Advanced Biopolymers S.r.l., Brindisi (IT)

( * ) Notice: Subject to any disclaimer, the term of this patent is extended or adjusted under 35 U.S.C. 154(b) by 0 days.

(21) Appl. No.: 09/719,200

(22) PCT Filed: Jun. 16, 1999

(86) PCT No.: PCT/EP99/04167

§ 371 (c)(1), (2), (4) Date: Dec. 8, 2000

(87) PCT Pub. No.: WO99/65534

PCT Pub. Date: Dec. 23, 1999

(30) Foreign Application Priority Data

Jun. 17, 1998 (IT) .......................................... PD98A0149

(51) Int. Cl.[7] ........................ A61K 31/715; C08B 37/00
(52) U.S. Cl. ........................................ 514/54; 536/55.1
(58) Field of Search ............................ 536/55.1; 514/54

(56) References Cited

U.S. PATENT DOCUMENTS

| | | | |
|---|---|---|---|
| 4,851,521 A | 7/1989 | della Valle et al. | 536/55.1 |
| 4,957,744 A | 9/1990 | della Valle et al. | 424/401 |
| 5,520,916 A | 5/1996 | Dorigatti et al. | 424/402 |
| 5,676,964 A | 10/1997 | Della Valle et al. | 424/423 |

FOREIGN PATENT DOCUMENTS

| | | |
|---|---|---|
| EP | 0 462 426 B1 | 8/1997 |
| WO | WO 93 11803 | 6/1993 |
| WO | 9311803 | 6/1993 |
| WO | 95/25751 | 9/1995 |
| WO | 9633750 | 10/1996 |
| WO | WO 96 33750 | 10/1996 |
| WO | 96/35720 | 11/1996 |
| WO | 9635720 | 11/1996 |
| WO | WO 96 35720 | 11/1996 |
| WO | 9718842 | 5/1997 |
| WO | 97/18842 | 5/1997 |
| WO | WO 97 18842 | 5/1997 |
| WO | 98/45335 | 10/1998 |
| WO | WO 98 56897 | 12/1998 |
| WO | 9856897 | 12/1998 |

OTHER PUBLICATIONS

Surgery, "A Comparison of Prosthetic Materials Used ot Repair Abdominal Wall Defects" by Dr. Scott d. Jenkens, Dr. Thomas W. Klamer, Dr. John J. Parteka and Dr. Robert E. Condon, Aug. 1983, pp. 392–398.

Lin–Shu Liu: "An Osteoconductive collagen/hyaluronate marix for bone regeneration" BioMaterials, GB, Elsevier Science Publishers BV., Barking, vol. 20, No. 20 p. 1097–1108.

Cortivo R et al: "In Vitro studies on Biocompatibility of Hyaluronic Acid Esters" BioMaterials, GB, Elsevier Science Publisher BV., Barking, vol. 12, No. 8, p. 727–730.

Primary Examiner—Peter O'Sullivan
(74) Attorney, Agent, or Firm—Hedman & Costigan, P.C.

(57) ABSTRACT

A three-dimensional prosthesis is described in the shape of a body part comprising at least one three-dimensional matrix having an essentially fibrous or porous structure and containing a hyaluronic acid derivative, said prosthesis, contains at least two of said three-dimensional matrixes, the first of said three-dimensional matrixes incorporating or being adhered to the second and possible further matrixes, said three-dimensional matrix(es) optionally inicorporating and/ or being adhered to a bidimensional perforated matrix and containing a hyaluronic acid derivative. This prosthesis is used for reconstruction of human or animal body part.

29 Claims, No Drawings

THREE-DIMENSIONAL PROSTHESES CONTAINING HYALURONIC ACID DERIVATIVES

This application is a 371 of PCT/EP99/04167, filed Jun. 16, 1999.

FIELD OF THE INVENTION

The present invention describes three-dimensional prostheses and process for their preparation.

Three-dimensional prostheses of the present invention can be used alone or in association with pharmaceutically or biologically active substances, and can be used as such or can act as scaffolds for cell cultures. Said three-dimensional prostheses are useful for reconstruction of human or animal body part, surgery or neurosurgery.

TECHNICAL BACKGROUND

Prostheses intended for implant are usually made of synthetic materials or natural, treated materials.

Defects of the body walls, such as the abdominal walls, that cannot be repaired by autogenous tissues because of the extent of the trauma, may be treated, for example, with synthetic meshes.

Indeed, the materials normally used for prostheses to reinforce or repair traumatised abdominal walls are tantalum gauze, stainless steel meshes, polypropylene tissues, microporous e-PTFE, polygalactin 910, polyester, polyglycolic acid, cross-linked bovine pericardium.

It has not, however, been possible to date to obtain satisfactory recovery of damaged tissue or impaired organs by implanting artificial prostheses such as cardiovascular or bone prostheses made of synthetic polymers or metals. Indeed, these types of prostheses are prone to provoke inflammatory reactions in the host, they rarely integrate easily with the surrounding microenvironment, they cause the formation of fibroses and they are subject to mechanical wear and tear, thus requiring regular checks.

One alternative is to transplant autologous tissues or organs, or more frequently allogenic or even xenogenic ones. This solution has various disadvantages, such as immunogenic reactions, infections and the dearth of donors. Recently, a new biomedical practice known as tissue engineering has been gaining ground. By this means, tissues similar to those of the organism can be obtained by taking cells by minor biopsies, expanding them in culture and cultivating them on biodegradable scaffolds. Such tissues, for example skin, cartilage and bone, are created in vitro and then grafted onto the patient (EP 0462426, WO 97/18842).

Other tissues for which work is in progress to improve the reconstruction techniques are those of the visible parts or appendices of the human body such as the ears, nose, nipples, lips and breasts.

It has proved particularly difficult, to date, to reconstruct the auricula because of the difficulties linked with the anatomical location of the ear, where any asymmetries of size, shape or position are instantly noticeable. Moreover, it is difficult to reproduce the complex form of irregularly-shaped cartilage covered with skin.

Various techniques are used to reconstruct the ear, according to the severity of the trauma.

In cases where only part of the ear has been severed, pieces of the same ear or the surrounding tissues are used to reconstruct the damaged part, or portions of intercostal cartilage are grafted into place and then covered with strips of adjacent skin, so that the implant can become vascularised.

When the auricula has been almost completely severed, synthetic auricular prostheses can be used. These have numerous disadvantages, however, such as the need for daily care, damage to the surrounding skin both on account of the direct contact with the prosthesis and because of the strong adhesives required to fix them in place. Some prostheses, however, are directly implanted into the bone. Another reconstruction method consists in increasing the volume of tissue still available by means of expanders.

Lastly, a very complex surgical technique is sometimes used that involves several steps carried out at different times, which gives acceptable results only after months of treatment.

Briefly, this technique consists in taking a portion of intercostal cartilage from the patient and shaping it into a form resembling the outer ear. The cartilage is usually first implanted subcutaneously on the forearm or back in order for it to become vascularised, and is removed several times for reshaping.

When the implant has reached a satisfactory stage of maturity, it is implanted in place of the ear and covered with a strip of adjacent skin.

Lastly, the patient has to undergo further operations to improve the aesthetic quality of the implant.

Besides the disadvantage of having to perform so many different operations on the patient, this technique involves the use of intercostal cartilage which has different characteristics from that of the ear, such as its lesser elasticity.

Unfortunately, these prostheses often do not take and degenerate to the point of generalised necrosis and failure of the transplant or, more rarely, the cartilage may transform into bony tissue (calcification).

The ideal material for such prostheses is therefore chemically inert, non-carcinogenic, able to stand up to mechanical stress and able to be shaped into the desired form, sterilizable, not prone to physical modification by the tissue fluids, they must not induce inflammatory, immunological, allergic or hypersensitivity reactions and they must not promote visceral adhesions (Jenkins S. D. et al. Surgery 94 (2); 392–398, 1983).

SUMMARY OF THE INVENTION

The present invention describes a three-dimensional prosthesis in the shape of a body part comprising at least one three-dimensional matrix having an essentially fibrous or porous structure and containing at least one hyaluronic acid derivative, said prosthesis, when contains at least two of said three-dimensional matrixes, the first of said three-dimensional matrixes incorporating or being adhered to the second and possible further matrixes, said three-dimensional matrix(es) optionally incorporating and/or being adhered to a bidimensional perforated matrix and containing a hyaluronic acid derivative.

Said three-dimensional prostheses further comprise cells chosen from the group consisting of autologous or endogenous mature or mesenchymal cells, or complex systems of mesenchymal and different type of mature cell types.

DETAILED DESCRIPTION OF THE INVENTION

According to a preferred embodiment the prosthesis of the present invention comprises a matrix (A) selected from the group consisting of:

A1. A three-dimensional matrix having an essentially fibrous structure

A2. A three-dimensional matrix having an essentially porous structure

A3. A bidimensional perforated matrix said matrix (A) incorporating and/or being adhered to a matrix selected from the group consisting of B. A three-dimensional matrix having an essentially porous structure in case (A) is (A1) or (A3)

C. A three-dimensional matrix having an essentially fibrous structure in case (A) is (A2) or (A3)

D. A bidimensional perforated matrix in case (A) is (A1) or (A2)

said matrix (A), (B), (C), (D) comprising at least one hyaluronic acid derivative.

Of the hyaluronic acid derivatives to be used in the preparation of the three-dimensional prostheses according to the present invention, the following are the ones of choice:

hyaluronic acid esters wherein a part or all of the carboxy functions are esterified with alcohols of the aliphatic, aromatic, arylaliphatic, cycloaliphatic, heterocyclic series (EP 0216453 B1 entirely incorporated by reference), especially with benzyl alcohol;

cross-linked esters of hyaluronic acid wherein part or all of the carboxy groups are esterified with the alcoholic functions of the same polysaccharide chain or of other chains (EP 0341745 B1 entirely incorporated by reference);

cross-linked compounds of hyaluronic acid wherein part or all of the carboxy groups are esterified with polyalcohols of the aliphatic, aromatic, arylaliphatic, cycloaliphatic, heterocyclic series, generating cross-linking by means of spacer chains (EP 0265116 B1 entirely incorporated by reference);

hemiesters of succinic acid or heavy metal salts of the hemiester of succinic acid with hyaluronic acid or with partial or total esters of hyaluronic acid (WO 96/357207 entirely incorporated by reference);

O-sulphated derivatives (WO 95125751 entirely incorporated by reference) or N-sulphated derivatives (PCT/EP98/01973 entirely incorporated by reference);

quaternary ammonium salts, such as salts with tetrabutylammonium and phenyltrimethylammonium, of hyaluronic acid or a hyaluronic acid derivative selected from the group consisting of N-sulphated hyaluronic acid, O-sulphated hyaluronic acid, the hemiesters of succinic acid with hyaluronic acid and optionally partially salified with heavy metals.

The matrixes (A1) and (C) having an essentially fibrous structure contained in the prostheses according to the present invention are preferably in the form of non woven tissue or in the form of meshes.

The non woven tissue containing hyaluronic acid derivatives is prepared as described in U.S. Pat. No. 5,520,916 we entirely incorporate herewith by reference. Such prostheses have the advantage of being made easily into any form, however complex, and moreover according to the chemical structure of the hyaluronic acid derivative used and according to the degree of esterification have the advantage of having tensile strength and degradation times that can be adjusted according to the requirement of the area to be reconstructed.

Said prostheses may also contain associations of natural, semisynthetic and synthetic polymers.

Natural polymers that can be used are, for example, collagen, coprecipitates of collagen and glycosaminoglycans, cellulose, polysaccharides in the form of gels such as chitin, chitosan, pectin or pectic acid, agar, agarose, xanthane, gellan, alginic acid or the alginates, polymannan or polyglycans, starch, natural gums. The semisynthetic polymers, for example, can be chosen from the group consisting of collagen cross-linked with agents such as aldehydes or precursors of the same, dicarboxylic acids or their halogenides, diamines, derivatives of cellulose, hyaluronic acid, chitin, chitosan, gellan, xanthane, pectin or pectic acid, polyglycans, polymannan, agar, agarose, natural gum, glycosaminoglycans. Lastly, examples of synthetic polymers that can be used are, for example, polylactic acid, polyglycolic acid or copolymers of the same or their derivatives, polydioxanes, polyphosphazenes, polysulphonic resins, polyurethanes, PTFE.

As the prostheses according to the present invention are constituted by hyaluronic acid derivatives, they are able to stimulate tissue regeneration and cell growth on their surfaces.

Said prostheses, indeed, can be used as such or as scaffolds for cell cultures for the reconstruction of human or animal body parts which have been damaged or are missing following trauma or as a result of congenital defects.

In the former case, the endogenous cells colonise the prosthesis in vivo, while in the latter case autologous cells are cultivated on the prosthesis before grafting.

It is also possible to cultivate mature or mesenchymal cells that can be made to differentiate into the desired cell line; complex systems of different cell types can also be cultivated.

The prostheses according to the present invention may also contain pharmaceutically or biologically active substances, such as anti-inflammatory agents, antibiotics, growth factors, antimicotic, antimicrobial and antiviral agents.

Said products, alone or containing cell cultures, can be used in general, internal, otorhinolaryngological, plastic, aesthetic, oncological, orthopaedic, cardiovascular, gynaecological and abdominal surgery and neurosurgery.

The body parts that can be reconstructed by means of the prostheses are, for example, the auricula, the nose, the nasal septum, the pharynx, the larynx, the trachea, joints such as the knuckles, the temporomandibular joints, bone structures and, moreover, eye sockets, cardiac valves, blood vessels, nipples, navels, internal organs and their parts and the secondary sexual organs.

In the case of reconstruction of a human body part with a complex form such as the auricula, the product must meet the following requisites:

it must be of the same anatomical shape as the part to be reconstructed, and be of the correct size for the patient;

it must have a surface on which the cells can multiply, adapting themselves to the form of the prosthesis;

they must be biodegradable and at the same time guarantee that the structure of the scaffold stays the same for as long as it takes for the new tissue to be formed. In order to produce at an industrial level prostheses with a complex form constituted by at least one hyaluronic acid derivative, that do not degrade rapidly when in contact with the, body fluids or in cell culture solutions and that meet the above said requisites, it has been necessary to devise an innovative working process by which to establish chemical-physical interactions between the molecules of the hyaluronic acid derivative, so that the prosthesis is firmly set in the desired form.

In particular when the matrix A is A1 and said matrix incorporates matrix B, the process of the present invention comprises the following steps:

a) lining a mould with a layer of non woven tissue comprising a hyaluronic acid derivative b) impregnating said non woven tissue in the mould with an aqueous solution of a quaternary ammonium salt of hyaluronic acid or of a hyaluronic acid derivative such as O-sulphated hyaluronic acid or N-sulphated hyaluronic acid, the hemiesters of hyaluronic acid with succinic acid and optionally their salts with heavy metals c) freeze-drying the content of the mould thereby obtaining prostheses having the matrix A1 incorporating the matrix B consisting of the ammonium salts for example, tetrabutylammonium salt of hyaluronic acid or phenyltrimethylammonium salt of hyaluronic acid, or of a hyaluronic acid derivative such as 0sulphated hyaluronic acid or N-sulphated hyaluronic acid, the hemiesters of hyaluronic acid with succinic acid and optionally their salts with heavy metals.

d) optionally converting the ammonium salt contained in the prostheses coming from step (c) into a hyaluronic acid derivative selected from partial or total ester of hyaluronic acid with alcohols of the aliphatic, aromatic, arylaliphatic, cycloaliphatic or heterocyclic series, crosslinked esters of hyaluronic acid wherein part or all of the carboxy groups are esterified with alcoholic functions of the same or a different polysaccharide chain or other chains, crosslinked derivative of hyaluronic acid, wherein part or all of the carboxy groups are esterified with polyalcohols of the aliphatic, aromatic, arylaliphatic, cycloaliphatic or heterocyclic series generating crosslinking by means of spacer chains, hemiester of succinic acid or heavy metal salt of hemiester of succinic acid with partial or total ester of hyaluronic acid, N-sulphated or 0sulphated partial or total ester of hyaluronic acid.

e) optionally freeze drying the product coming from (d);

When the matrix A is A2 or the product obtained from above defined step c or d of the preceding process and is adhered to matrix C, the process comprises the following steps:

a') applying a thin layer of an aqueous solution of a quaternary ammonium salt of hyaluronic acid or of a derivative selected from O-sulphated hyaluronic acid (WO 95/25751) or N-sulphated hyaluronic acid (PCT/EP98/01973), hemiesters of hyaluronic acid with succinic acid and optionally their salts with heavy metals (WO96/357207) to the same or a different freeze-dried quaternary ammonium salt b') adhering to the mixture coming from step (a') a layer of non woven tissue comprising a hyaluronic acid derivative c') freeze-drying the mixture coming from step (b') thereby obtaining prostheses wherein the matrix A is A2 and consists of an ammonium such as quaternary ammonium salt of hyaluronic acid or of a derivative thereof which has not yet been esterified such as O-sulphated hyaluronic acid (WO 95/25751) or N-sulphated hyaluronic acid (PCT/EP98/01973), the hemiesters of hyaluronic acid with succinic acid and optionally their salts with heavy metals (WO96/357207) adhering to the matrix C d') optionally converting the ammonium salt contained in the prostheses coming from step (c') with a hyaluronic acid derivative selected from partial or total ester of hyaluronic acid with alcohols of the aliphatic, aromatic, arylaliphatic, cycloaliphatic or heterocyclic series, crosslinked esters of hyaluronic acid wherein part or all of the carboxy groups are esterified with alcoholic functions of the same or a different polysaccharide chain or other chains, crosslinked derivative of hyaluronic acid, wherein part or all of the carboxy groups are esterified with polyalcohols of the aliphatic, aromatic, arylaliphatic, cycloaliphatic or heterocyclic series generating crosslinking by means of spacer chains, hemiester of succinic acid or heavy metal salt of hemiester of succinic acid with partial or total ester of hyaluronic acid, N-sulphated or O-sulphated partial or total ester of hyaluronic acid e) optionally freeze drying the product coming from (d'); and When matrix (A) is (A2) or the product obtained from above defined step c or d coming from the first process and is adhered to matrix (C), the process comprises the following steps:

a'') applying a thin layer of a solution of a hyaluronic acid derivative in a suitable aqueous or organic solvent, such as DMSO, said hyaluronic acid derivative being selected from partial or total ester of hyaluronic acid with alcohol of the aliphatic, aromatic, arylaliphatic, cycloaliphatic or heterocyclic series, crosslinked esters of hyaluronic acid wherein part or all of the carboxy groups are esterified with alcoholic functions of the same or a different polysaccharide chain or other chains, crosslinked derivatives of hyaluronic acid, wherein part or all of the carboxy groups are esterified with polyalcohols of the aliphatic, aromatic, arylaliphatic, cycloaliphatic or heterocyclic series generating crosslinking by means of spacer chains, hemiester of succinic acid or heavy metal salt of hemiester of succinic acid with partial or total ester of hyaluronic acid, N-sulphated or O-sulphated partial or total ester of hyaluronic acid b'') applying a non woven tissue comprising a hyaluronic acid derivative to the freeze dried product coming from step (a'')

c'') freeze-drying the product coming from step (b'').

In case the prosthesis according to the present invention contains at least one porous matrix consisting of a hyaluronic acid derivative, the process comprises the following steps:

a''') pouring an aqueous solution of a quaternary ammonium salt of hyaluronic acid or of a derivative selected from O-sulphated hyaluronic acid, N-sulphated hyaluronic acid and hemiesters of hyaluronic acid with succinic acid and optionally their salts with heavy metals into a mould having the shape of the body part to be reconstructed b''') freeze drying the aqueous solution in the mould c''') detaching the freeze dried product from the mould and converting the freeze dried ammonium salts into at least one hyaluronic acid derivative selected from partial or total ester of hyaluronic acid with alcohols of the aliphatic, aromatic, arylaliphatic, cycloaliphatic or heterocyclic series, crosslinked esters of hyaluronic acid wherein part or all of the carboxy groups are esterified with alcoholic functions of the same or a different polysaccharide chain or other chains, crosslinked derivative of hyaluronic acid, wherein part or all of the carboxy groups are esterified with polyalcohols of the aliphatic, aromatic, arylaliphatic, cycloaliphatic or heterocyclic series generating crosslinking by means of spacer chains, hemiester of succinic acid or heavy metal salt of hemiester of succinic acid with partial or total ester of hyaluronic acid, N-sulphated or O-sulphated partial or total ester of hyaluronic acid d''') freeze drying the product coming from the preceding step in the mould

EXAMPLE 1

Preparation of the Phenyltrimethylammonium Salt of Hyaluronic Acid

Sixty-nine grams of sodium hyaluronate is solubilised in 4 l of water and passed through a column previously filled with Dowex Resin M15 in tetrabutylammonium form. This is freeze-dried, after which 100 g of hyaluronic acid tetrabutylammonium salt is obtained.

One hundred and fifty grams of hyaluronic acid tetrabutylammonium salt (HA-TBA) and 225 g of phenyltrimethylammonium chloride are solubilised in a mixture constituted by 2 l of water and 3 l of acetone (40/60 mixture).

Fifteen liters of acetone are added and a precipitate of hyaluronic acid phenyltrimethylammonium salt is obtained.

The precipitate is washed several times with acetone and dried at a temperature of about 35° C. for 72 hours (Yield: 125 g).

EXAMPLE 2

Preparation of a Prosthesis for the Reconstruction of the Auricula Constituted by the Total Benzyl Ester of Hyaluronic Acid (HYAFF®11)

A hollow mould is prepared in the shape of the auricula, made of polymers used in dentistry. The shape of the missing ear is reconstructed by a computerised system using a mirror image of the other ear.

The mould is lined with a layer of HYAFF®11 in the form of a non-woven tissue, fitting it closely to the shape of the mould.

The non-woven tissue is impregnated with 15 ml of an aqueous solution of hyaluronic acid salt with phenyltrimethylammonium at a concentration of 70 mg/ml and this is freeze-dried.

The solid intermediate product in the form of an auricula, constituted by the salt of hyaluronic acid with phenyltrimethylammonium, that contains the non-woven HYAFF®11 tissue, is removed from the mould and exposed to an esterification reaction in the heterogeneous phase.

The material is placed in 0.3 liters of acetone per gram of intermediate product, and then 4 grams of tetrabutylammonium bromide and 3 ml of benzylbromide are added. The mixture is kept at boiling point for 12 hours.

The product is repeatedly washed with a solution of ethanol and water in a ratio of 1:1 and containing 3% of sodium chloride, after which it is washed with water. Lastly, the product is put back into the mould and freeze-dried.

EXAMPLE 3

Preparation of a Prosthesis for the Reconstruction of the Auricula Constituted by the Total Benzyl Ester of Hyaluronic Acid (HYAFF®11)

A hollow mould is prepared in the shape of the auricula, made of polymers used in dentistry. The shape of the missing ear is reconstructed by a computerised system using a mirror image of the other ear.

The mould is lined with a layer of HYAFF®11 in the form of a non-woven tissue, fitting it closely to the shape of the mould.

The non-woven tissue is impregnated with 15 ml of an aqueous solution of hyaluronic acid salt with tetrabutylammonium at a concentration of 70 mg/ml and this is freeze-dried.

The solid intermediate product in the form of an auricula, constituted by the salt of hyaluronic acid with tetrabutylammonium, that contains the non-woven HYAFF®11 tissue, is removed from the mould and exposed to an esterification reaction in the heterogeneous phase.

The material is placed in 0.06 liters of acetone per gram of intermediate product, and then 4.2 grams of tetrabutylammonium bromide and 1.4 ml of benzylbromide are added.

The mixture is kept at boiling point for 12 hours.

The product is repeatedly washed with a solution of ethanol and water in a ratio of 1:1 and containing 3% of sodium chloride, after which it is washed with water. Lastly, the product is put back into the mould and freeze-dried.

EXAMPLE 4

Preparation of a Prosthesis for the Reconstruction of the Auricula Constituted by the Total Benzyl Ester of Hyaluronic Acid (HYAFF®11)

A hollow mould is prepared in the shape of the auricula, made of polymers used in dentistry. The shape of the missing ear is reconstructed by a computerised system using a mirror image of the other ear.

The mould is lined with a layer of HYAFF®11 in the form of a non-woven tissue, fitting it closely to the shape of the mould.

The non-woven tissue is impregnated with 15 ml of an aqueous solution of hyaluronic acid salt with tetrabutylammonium at a concentration of 70 mg/ml and this is freeze-dried.

The solid intermediate product in the form of an auricula, constituted by the salt of hyaluronic acid with tetrabutylammonium, that contains the non-woven HYAFF®11 tissue, is removed from the mould and exposed to an esterification reaction in the heterogeneous phase.

The material is placed in 0.06 liters of acetone per gram of intermediate product, and then 4.2 grams of tetrabutylammonium bromide and 1.4 ml of dodecyl bromide are added.

The mixture is kept at boiling point for 12 hours.

The product is repeatedly washed with a solution of ethanol and water in a ratio of 1:1 and containing 3% of sodium chloride, after which it is washed with water. Lastly, the product is put back into the mould and freeze-dried.

EXAMPLE 5

Preparation of a Prosthesis for the Reconstruction of the Auricula Constituted by the Total Benzyl Ester of Hyaluronic Acid (HYAFF®11) in the Form of a Non-woven Fabric Incorporated in Autocross-linked Hyaluronic Acid A hollow mould is prepared in the shape of the auricula, made of polymers used in dentistry. The shape of the missing ear is reconstructed by a computerised system using a mirror image of the other ear.

The mould is lined with a layer of HYAFF®11 in the form of a non-woven tissue, fitting it closely to the shape of the mould.

The non-woven tissue is impregnated with 15 ml of an aqueous solution of hyaluronic acid salt with tetrabutylammonium at a concentration of 70 mg/ml and this is freeze-dried.

The solid intermediate product in the form of an auricula, constituted by the salt of hyaluronic acid with tetrabutylammonium, that contains the non-woven HYAFF®11 tissue, is removed from the mould and exposed to an esterification reaction in the heterogeneous phase.

The material is placed in 1.5 liters of acetone per 10 grams of intermediate product, and then 70 grams of molecular sieve and 10 g of 2-chloro-1-methyl pyridinium iodide are added.

The mixture is kept at boiling point for 8 hours.

The product is washed first with acetone and then with an aqueous solution containing 3% sodium chloride and lastly with water.

EXAMPLE 6

Preparation of a Three-Dimensional Prosthesis Constituted by the Total Benzyl Ester of Hyaluronic Acid (HYAFF®11) With a Layer of Non-woven Fabric (HYAFF®11) Adhered to its Surface Method 1 Adhesion of a Layer of Non-woven Fabric (HYAFF®11) to the Product Before Esterification A thin layer of a solution of hyaluronic acid salt with tetrabutylammonium in water at a concentration of about 70 mg/ml is applied onto the surface of a freeze-dried product constituted by hyaluronic acid salt with tetrabutylammonium or with phenyltrimethylammonium, then a layer of non-woven fabric (HYAFF®11) is applied. The product is replaced in the mould, brought to a temperature of 40° C. and freeze-dried. The product is then exposed to an esterification reaction, as in the previous examples.

Method 1A The same method with the same ingredients described in Method 1 is repeated without adding the layer of non woven fabric.

Method 2 Adhesion of a Layer of Non-Woven Fabric (HYAFF®11) to the Esterified Product A thin layer of a solution of HYAFF®11 in dimethylsulfoxide (DMSO) at a concentration of about 180 mg/ml is applied to the surface of the product constituted by HYAFF®11, after which a layer of non-woven fabric (HYAFF®11) is applied. The product is then immersed in ethyl alcohol for at least 30 minutes. It is then washed repeatedly with ethanol and then with water. The product is placed in the mould and freeze-dried.

Cell Culture on an Auricular Prosthesis

A biopsy of nasal cartilage is taken by the standard procedure.

The specimen of cartilage is disintegrated by enzymatic digestion with 0.25% trypsin and 0.02% EDTA, incubated at 37° C. with 5% carbon dioxide for 15 minutes, followed by a second session of enzymatic digestion with a solution of 0.1% collagenase.

The specimen is stirred and incubated for about 16 hours at 37° C.

Subsequently, any fragments of residue tissue are separated by centrifugation and the supernatant is removed.

Enzymatic reaction is interrupted by adding culture medium enriched with 10% foetal bovine serum (FBS) or with Dulbecco's minimal essential medium (DMEM) enriched with 10% FBS.

Approximately $1\times10^6/cm^2$ of the cells are resuspended in a culture medium containing growth factors and seeded on the biomaterial in a dish measuring 100 mm in diameter.

After three hours' incubation at 37° C., 10 ml of culture medium containing growth factor is added. The culture is incubated and fresh medium added 48 hours after seeding and then every 48–72 hours.

The invention being thus described, it is clear that these methods can be modified in various ways. Said modifications must not be considered as divergences from the spirit and purposes of the invention, and any modification that would appear evident to an expert in the field comes within the scope of the following claims:

What is claimed is:

1. A three-dimensional prosthesis in the shape of a body part comprising at least one three-dimensional matrix having an essentially fibrous or porous structure and containing at least one hyaluronic acid derivative, said prosthesis, when containing at least two of said three-dimensional matrices, the first of said matrices, incorporating and/or being adhered to the second and possible further matrices, said three-dimensional matrix(ces) optionally incorporating and/or being adhered to a bi-dimensional perforated matrix containing a hyaluronic acid derivative.

2. The three-dimensional prosthesis according to claim 1, comprising a matrix (A) selected from the group consisting of:

A1. A three-dimensional matrix having an essentially fibrous structure

A2. A three-dimensional matrix having an essentially porous structure

A3. A bidimensional perforated matrix said matrix (A) incorporating or being adhered to a matrix selected from the group consisting of B. A three-dimensional matrix having an essentially porous structure in case (A) is (A1) or (A3)

C. A three-dimensional matrix having an essentially fibrous structure in case (A) is (A2) or (A3)

D. A bidimensional perforated matrix in case (A) is (A1) or (A2)

said matrix (A), (B), (C), (D) comprising at least one hyaluronic acid derivative.

3. The three-dimensional prosthesis according to claim 1, further comprising cells chosen from the group consisting of autologous or endogenous mature or mesenchymal cells, or complex systems of mesenchymal and different type of mature cell types.

4. The three-dimensional prosthesis according to claim 1, further comprising natural, semisynthetic and synthetic polymers.

5. The three-dimensional prosthesis according to claim 4, wherein the natural polymers are chosen from the group consisting of collagen, coprecipitates of collagen and glycosaminoglycans, cellulose, polysaccharides in the form of gels such as chitin, chitosan, pectin or pectic acid, agar, agarose, xanthane, gellan, alginic acid or the alginates, polymannan or polyglycans, starch, natural gums.

6. The three-dimensional prosthesis according to claim 4, wherein the semisynthetic polymers are chosen from the group consisting of collagen cross-linked with agents such as aldehydes or precursors of the same, dicarboxylic acids or the halogenides thereof, diamines, derivatives of cellulose, hyaluronic acid, chitin or chitosan, gellan, xanthane, pectin or pectic acid, polyglycans, polymannan, agar, agarose, natural gum and glycosaminoglycans.

7. The three-dimensional prosthesis according to claim 4, wherein the synthetic polymers are chosen from the group consisting of polylactic acid, polyglycolic acid or copolymers of the same or their derivatives, polydioxans, polyphosphazenes, polysulphonic resins, polyurethanes, PTFE.

8. The three-dimensional prosthesis according to claim 2, wherein at least one of said matrices (A), (B), (C) and (D) consists of at least one hyaluronic acid derivative.

9. The three-dimensional prosthesis according to claim 2, in which said matrix A1 and C are selected from the group consisting of meshes or non woven tissue.

10. The three-dimensional prosthesis according to claim 1, wherein the matrix (A2) and (B) are obtained by freeze drying process.

11. The three-dimensional prosthesis according to claim 1, wherein said bidimensional perforated matrix is obtained by perforating a bidimensional membrane having a continuous structure.

12. The three-dimensional prosthesis according to claim 1, in which said hyaluronic acid derivative is chosen from the group consisting of esters of hyaluronic acid wherein part or all of the carboxy functions are esterified with alcohols of the aliphatic, aromatic, arylaliphatic, cycloaliphatic or heterocyclic series.

13. The three-dimensional prosthesis according to claim 12, in which said ester of hyaluronic acid is the benzyl ester of hyaluronic acid.

14. The three-dimensional prosthesis according to claim 1, wherein the hyaluronic acid derivative is chosen from the group consisting of cross-linked esters of hyaluronic acid wherein part or all of the carboxy groups are esterified with the alcoholic functions of the same or a different polysaccharide chain or other chains.

15. The three-dimensional prosthesis according to claim 1, wherein the hyaluronic acid derivative is chosen from the group consisting of crosslinked compounds of hyaluronic acid wherein part or all of the carboxy groups are esterified with polyalcohols of the aliphatic, aromatic, arylaliphatic, cycloaliphatic or heterocyclic series generating cross linking by means of spacer chains.

16. The three-dimensional prosthesis according to claim 1, wherein the hyaluronic acid derivative is chosen from the group consisting of the hemiesters of succinic acid or heavy metal salts of the hemiester of succinic acid with partial or total esters of hyaluronic acid.

17. The three-dimensional prosthesis according to claim 1, wherein the hyaluronic acid derivative is chosen from the group consisting of the partial or total esters of O-sulphated or N-sulphated derivatives.

18. The three-dimensional prosthesis according to claim 1, wherein the hyaluronic acid derivative is a quaternary ammonium salt of hyaluronic acid or a hyaluronic acid derivative selected from the group consisting of N-sulphated hyaluronic acid, O-sulphated hyaluronic acid, the hemiesters of succinic acid with hyaluronic acid and optionally partially salified with heavy metals.

19. The three-dimensional prosthesis according to claim 1, in association with pharmaceutically or biologically active substances.

20. The three-dimensional prosthesis according to claim 19, wherein the pharmaceutically or biologically active substances are selected from the group consisting of anti-inflammatory agents, antibiotics, growth factors, antimicotics, antimicrobials, antiviral agents.

21. The three-dimensional prosthesis according to claim 1, for reconstruction of human or animal body parts.

22. The three-dimensional prosthesis according to claim 21, wherein the body parts are the auricula, nose, nasal septum, pharynx, larynx, trachea, joints, bone structures, eye socket, cardiac valves, blood vessels, nipple, navel, internal organs and their parts, or the secondary sexual organs.

23. The three-dimensional prosthesis according to claim 21, wherein said body part is the auricula.

24. The three-dimensional prosthesis according to claim 21, wherein said body parts are knuckles or temporomandibular joint.

25. The three-dimensional prosthesis according to claim 1, for use in general, internal, otorhinolaryngological, plastic, aesthetic, oncological, orthopaedic, cardiovascular, gynaecological and abdominal surgery and neurosurgery.

26. A process for preparing a three-dimensional prosthesis comprising a three-dimensional matrix A1 having an essentially fibrous structure incorporating a three-dimensional matrix B having an essentially porous structure, said matrices A1 and B comprising at least one hyaluronic acid derivative, said process comprising the following steps:
  a) lining a mold with a layer of non woven tissue comprising a hyaluronic acid derivative;
  b) impregnating said non woven tissue in the mold with an aqueous solution of a quaternary ammonium salt of hyaluronic acid or of a hyaluronic acid derivative selected from the group consisting of N-sulphated hyaluronic acid, O-sulphated hyaluronic acid, the hemiesters of succinic acid with hyaluronic acid and optionally partially salified with heavy metals;
  c) freeze-drying the content of the mold thereby obtaining prostheses having the matrix A1 incorporating the matrix B consisting of a quaternary ammonium salt of hyaluronic acid or a hyaluronic acid derivative as defined above in item b);
  d) optionally converting the quaternary ammonium salt contained in the prostheses coming from step (c) into a hyaluronic acid derivative chosen from the group consisting of esters of hyaluronic acid wherein part or all of the carboxy functions are esterified with alcohols of the aliphatic, aromatic, arylaliphatic, cycloaliphatic or heterocyclic series, and cross-linked esters of hyaluronic acid wherein part or all of the carboxy groups are esterified with the alcoholic functions of the same or a different polysaccharide chain or other chains;
  e) freeze-drying the product coming from (d).

27. A process for preparing a three-dimensional prosthesis comprising a three-dimensional matrix A2 having an essentially porous structure being adhered to a three-dimensional matrix C having an essentially fibrous structure, said matrices A2 and C, comprising at least one hyaluronic acid derivative, said process comprising the following steps:

a') applying a thin layer of an aqueous solution of a quaternary ammonium salt of hyaluronic acid or of a hyaluronic acid derivative selected from the group consisting of N-sulphated hyaluronic acid, O-sulphated hyaluronic acid, the hemiesters of succinic acid with hyaluronic acid and optionally partially salified with heavy metals, to the same or different freeze-dried quaternary ammonium salt of hyaluronic acid or of hyaluronic acid derivative as defined above;
  b') adhering to the mixture coming from step (a') a layer of non woven tissue comprising a hyaluronic acid derivative;
  c') freeze-drying the mixture coming from step (b') thereby obtaining prostheses wherein the matrix A2 consists of a quaternary ammonium salt as defined above in item a'), adhering to matrix C;

d') optionally converting the ammonium salt contained in the prostheses coming from step (c') into a hyaluronic acid derivative chosen from the group consisting of esters of hyaluronic acid wherein part or all of the carboxy functions are esterified with alcohols of the aliphatic, aromatic, arylaliphatic, cycloaliphatic or heterocyclic series, and cross-linked esters of hyaluronic acid wherein part or all of the carboxy groups are esterified with the alcoholic functions of the same or a different polysaccharide chain or other chains;

e') freeze drying the product coming from (d').

28. A process for preparing a three-dimensional prosthesis comprising a three-dimensional matrix A2 having an essentially porous structure adhered to a three-dimensional matrix C having an essentially fibrous structure, said matrices A2 and C comprising at least one hyaluronic acid derivative, said process comprising the following steps:

a") applying a thin layer of a solution of a hyaluronic acid derivative in a suitable aqueous or organic solvent, said hyaluronic acid derivative being chosen from the group consisting of esters of hyaluronic acid wherein part or all of the carboxy functions are esterified with alcohols of the aliphatic, aromatic, arylaliphatic, cycloaliphatic or heterocyclic series, and cross-linked esters of hyaluronic acid wherein part or all of the carboxy groups are esterified with the alcoholic functions of the same or a different polysaccharide chain or other chains;

b") applying to the freeze dried product coming from step (a") a non woven tissue comprising a hyaluronic acid d derivative;

c") freeze-drying the product coming from step (b").

29. A process for preparing a three-dimensional prosthesis according to claim 1 containing at least one porous matrix consisting of a hyaluronic acid derivative, comprising the following steps:

a''')pouring an aqueous solution of a quaternary ammonium salt of hyaluronic acid or of a hyaluronic acid derivative selected from the group consisting of N-sulphated hyaluronic acid, O-sulphated hyaluronic acid, the hemiesters of succinic acid with hyaluronic acid and optionally partially salified with heavy metals, into a mold having the shape of the body part to be reconstructed;

b''') freeze-drying the aqueous solution in the;

c''') detaching the freeze dried product from the mold and converting the freeze dried ammonium salts of hyaluronic acid or of a hyaluronic acid derivative as defined above, into at least one hyaluronic acid derivative chosen from the group consisting of esters of hyaluronic acid wherein part or all of the carboxy functions are esterified with alcohols of the aliphatic, aromatic, arylaliphatic, cycloaliphatic or heterocyclic series, and cross-linked esters of hyaluronic acid wherein part or all of the carboxy groups are esterified with the alcoholic functions of the same or a different polysaccharide chain or other chains;

d''') freeze drying the product, coming from the preceding step, in the mold.

* * * * *